(12) United States Patent
Sandhu et al.

(10) Patent No.: US 11,298,119 B2
(45) Date of Patent: Apr. 12, 2022

(54) SPINAL RETRACTOR AND METHOD OF USE THEREFOR

(71) Applicant: K2M, Inc., Leesburg, VA (US)

(72) Inventors: Faheem Sandhu, Washington, DC (US); Nick Padovani, Arlington, VA (US); Josh Rubin, Falls Church, VA (US); Robert J. Tokash, Stephens City, VA (US)

(73) Assignee: K2M, Inc., Leesburg, VA (US)

( * ) Notice: Subject to any disclaimer, the term of this patent is extended or adjusted under 35 U.S.C. 154(b) by 250 days.

(21) Appl. No.: 16/446,030

(22) Filed: Jun. 19, 2019

(65) Prior Publication Data

US 2019/0380691 A1   Dec. 19, 2019

Related U.S. Application Data

(60) Provisional application No. 62/686,895, filed on Jun. 19, 2018.

(51) Int. Cl.
*A61B 17/02* (2006.01)
*A61B 17/00* (2006.01)

(52) U.S. Cl.
CPC .... *A61B 17/025* (2013.01); *A61B 2017/0046* (2013.01); *A61B 2017/0256* (2013.01)

(58) Field of Classification Search
CPC ................................ A61B 17/025–2017/0256
See application file for complete search history.

(56) References Cited

U.S. PATENT DOCUMENTS

| | | | | |
|---|---|---|---|---|
| 5,928,139 A | * | 7/1999 | Koros | A61B 17/0206 600/205 |
| 7,326,177 B2 | * | 2/2008 | Williamson, IV | A61B 1/32 600/201 |
| 8,038,611 B2 | * | 10/2011 | Raymond | A61B 17/3417 600/231 |
| 8,409,087 B2 | * | 4/2013 | Ames | A61B 17/025 600/210 |
| 8,668,715 B2 | * | 3/2014 | Sandhu | A61B 17/7077 606/204 |
| 9,017,409 B2 | | 4/2015 | Wallenstein et al. | |
| 2007/0073110 A1 | * | 3/2007 | Larson | A61B 1/32 600/210 |

(Continued)

FOREIGN PATENT DOCUMENTS

WO   2008039247 A2   4/2008

*Primary Examiner* — Zade Coley
(74) *Attorney, Agent, or Firm* — Lerner, David, Littenberg, Krumholz & Mentlik, LLP

(57) ABSTRACT

A retractor system includes first and second fixation pins and a retractor assembly including first and second retractor bodies. Each of the first and second retractor bodies includes a main panel and extension panels extending from the main panel. Each of the first and second retractor bodies is transitionable between a first configuration, in which, each of the first and second retractor bodies is substantially flat, and a second configuration, in which, each of the first and second retractor bodies has a substantially U-shaped profile such that the extension panels oppose each other. The extension panels of the first retractor body are configured to selectively overlap the respective extension panels of the second retractor body when the first and second retractor bodies are in the second configuration.

8 Claims, 18 Drawing Sheets

(56) References Cited

U.S. PATENT DOCUMENTS

| | | | | |
|---|---|---|---|---|
| 2008/0214898 A1* | 9/2008 | Warren | ............... | A61B 17/02 600/210 |
| 2008/0255519 A1* | 10/2008 | Piskun | ............... | A61B 17/3423 604/174 |
| 2011/0034777 A1* | 2/2011 | Ames | ............... | A61B 17/025 600/206 |
| 2011/0313256 A1* | 12/2011 | Raymond | ............ | A61B 17/3421 600/231 |

* cited by examiner

SPINAL RETRACTOR AND METHOD OF USE THEREFOR

CROSS-REFERENCE TO RELATED APPLICATIONS

This application claims the benefit of the filing date of U.S. Provisional Patent Application No. 62/686,895 filed Jun. 19, 2018, the disclosure of which is hereby incorporated by reference herein in its entirety.

TECHNICAL FIELD

The present disclosure relates to a device for spinal surgery and, more particularly, to a device for retracting soft tissue.

BACKGROUND OF THE INVENTION

There has been considerable development of retractor devices that are adapted for use in minimally invasive procedures. Many of the recent developments are based on traditional types of retractor devices for open procedures such as table-mounted devices of various designs. These devices tend to be cumbersome and are not well adapted for use in small incisions. Standard hand-held retractor devices can be modified to fit the contours of these small incisions, but they require manual manipulation to maintain a desired placement, thereby occupying one hand of the clinician or requiring another person to assist the clinician during the procedure. Typical retractor devices are also positioned into the soft tissue and are levered back to hold the wound open, frequently requiring re-positioning if they dislodge, obstruct the clinician's view, or interfere with access to the surgical site.

In a spinal fusion, at least two vertebral bodies are rigidly connected using bone screws implanted into the respective vertebral bodies with a solid metal rod spanning the distance between the screws. The insertion of pedicle or facet screws is relatively straightforward and can be accomplished through a minimal incision. The difficulty arises upon the introduction of a length of rod into a very small incision with extremely limited access and visibility.

Therefore, a continuing need exists for a retractor device that works with current instruments to provide the retraction needed in a spinal procedure with an ease of use and without impairing a view of the surgical field.

BRIEF SUMMARY OF THE INVENTION

In accordance with an embodiment of the present disclosure, a retractor system includes first and second fixation pins and a retractor assembly including first and second retractor bodies. Each of the first and second retractor bodies includes a main panel and extension panels extending from the main panel. The main panel includes a sleeve defining a bore dimensioned to receive one of the first and second fixation pins. Each of the first and second retractor bodies is transitionable between a first configuration, in which, each of the first and second retractor bodies is substantially flat, and a second configuration, in which, each of the first and second retractor bodies has a substantially U-shaped profile such that the extension panels oppose each other. The extension panels of the first retractor body are configured to selectively overlap the respective extension panels of the second retractor body when the first and second retractor bodies are in the second configuration, whereby the main panels of the first and second retractor bodies are transitionable between a spaced apart position and an approximated position.

In an embodiment, the main panel may include a base portion and an extension portion extending proximally from the base portion. The extension portion may be more flexible than the base portion.

In another embodiment, the extension portion of the main panel may be formed of a resilient material.

In another embodiment, each extension panel may include a connecting portion and a retracting portion extending proximally from the connecting portion.

In yet another embodiment, the extension portion of the main panel and the retracting portions of the extension panels may be formed of a clear amorphous thermoplastic material.

In still yet another embodiment, each of the first and second retractor bodies may include living hinge portions interconnecting the main panel and the respective extension panels.

In still yet another embodiment, the living hinge portions may connect the base portion of the main panel and the respective connecting portions of the extension panels.

In still yet another embodiment, each of the first and second retractor bodies may define slits between the extension portion of the main panel and the respective retracting portions of the extension panels.

In an embodiment, the retracting portions of the extension panels may define a plurality of bores.

In an embodiment, the retractor system may further include a locking arm having an elongate member and a peg dimensioned to be received in overlapping bores of the retracting portions of the extension panels in order to securely lock the relative position of the first and second retractor bodies.

In another embodiment, the main panel, the extension panels, and the hinges may be monolithically formed.

In another embodiment, the main panel may define a curvature.

In yet another embodiment, the extension portion of the main panel may define a plurality of bores.

In still yet another embodiment, at least one of the first or second fixation pins may include a distal portion having threads configured to threadably engage a vertebral body and a proximal portion having a key feature configure to provide non-slip engagement with a driver to drive the at least one of the first or second fixation pins.

In accordance with another embodiment of the present disclosure, a retractor assembly includes first and second retractor bodies. Each of the first and second retractor bodies includes a main panel and extension panels interconnected by the main panel. The first and second retractor bodies are configured to oppose each other, thereby defining a working space therebetween. The extension panels of the first retractor body are configured to selectively overlap the respective extension panels of the second retractor body. The first and second retractor bodies are selectively transitionable between an expanded configuration and a contracted configuration.

In an embodiment, the main panel may include a sleeve defining a bore dimensioned to receive a fixation pin.

In an embodiment, the main panel may include a concave surface. The sleeve may extend from the concave surface.

In accordance with another embodiment of the present disclosure, a retractor system includes a fixation pin, an insertion instrument, and a retractor body. The insertion instrument includes a receiving body defining a cavity therein, and a handle extending from the receiving body. The retractor body includes a main panel and first and second plurality of extension panels. The main panel includes an arcuate surface configured to slidably receive the fixation pin therein. The arcuate surface has a sleeve configured to secure the fixation pin thereto. The first plurality of extension panels extends from a first side of the main panel. The second plurality of extension panels extends from a second side of the main panel. The retractor body is transitionable between a first configuration, in which, the main panel and the first and second plurality of extension panels are in a superposed relation, and a second configuration, in which, the main panel and the first and second plurality of extension panels form a substantially U-shaped profile such that the first and second plurality of extension panels oppose each other. The retractor body in the first configuration is configured to be received in the cavity of the receiving body of the insertion instrument.

In one aspect, the present disclosure relates to a retractor system. In one embodiment, a retractor system includes first and second fixation pins and a retractor assembly with first and second retractor bodies. The first retractor body includes a first main panel and first and second extension panels extending from the first main panel. The second retractor body includes a second main panel and third and fourth extension panels extending from the second main panel. The first and second main panels include a sleeve defining a bore dimensioned to receive one of the first and second fixation pins. The first and second retractor bodies are transitionable between a first configuration in which each of the first and second retractor bodies is substantially flat, and a second configuration in which the first and second extension panels are transverse to the first main panel and the third and fourth extension panels are transverse to the second main panel. In the second configuration, the extension panels of each retractor body oppose each other. The first and second extension panels are configured to overlap the third and fourth extension panels when the first and second retractor bodies are in the second configuration, whereby the first and second main panels are transitionable between a first position and a second position. The first and second main panels are closer to each other in the first position than in the second position.

In some embodiments, the first and second extension panels may be parallel to one another in the second configuration. In some embodiments, each of the first and second retractor bodies may have a substantially U-shaped profile in the second configuration. In some embodiments, the first and second extension panels may be configured to selectively overlap the respective third and fourth extension panels in predetermined increments in the second configuration. In some embodiments, each main panel may include a base portion and an extension portion extending proximally from the base portion, the extension portion being more flexible than the base portion. In some embodiments, the extension portion of each main panel may be formed of a resilient material. In some embodiments, each extension panel may include a connecting portion and a retracting portion extending proximally from the connecting portion. In some embodiments, the extension portion of each main panel and the retracting portions of each extension panel may be formed of a clear amorphous thermoplastic material. In some embodiments, each of the first and second retractor bodies may include living hinge portions interconnecting the main panel and the respective extension panels adjacent to the main panel. In some embodiments, the living hinge portions on each of the first and second retractor bodies may connect the base portion of the main panel and the respective connecting portions of the adjacent extension panels.

In some embodiments, each of the first and second retractor bodies may define slits between the extension portion of the main panel and the respective retracting portions of the adjacent extension panels. In some embodiments, the retracting portions of each of the extension panels may define a plurality of bores. In some embodiments, the system may include a locking arm having an elongate member and a peg dimensioned to be received in overlapping bores of the retracting portions of each of the extension panels in order to securely lock the relative position of the first and second retractor bodies. In some embodiments, the main panels, each of the extension panels, and the hinges may be monolithically formed. In some embodiments, at least one of the main panels may define a curvature. In some embodiments, the extension portion of each of the main panels may define a plurality of bores. In some embodiments, at least one of the first or second fixation pins may include a distal portion having threads configured to threadably engage a vertebral body and a proximal portion having a key feature configure to provide non-slip engagement with a driver to drive the at least one of the first or second fixation pins.

In another aspect, the present disclosure relates to a retractor assembly. In one embodiment, the retractor assembly includes first and second retractor bodies. Each of the first and second retractor bodies includes a main panel and extension panels that are interconnected by the main panel. The first and second retractor bodies are configured to oppose each other, thereby defining a working space therebetween. The extension panels of the first retractor body are configured to selectively overlap the respective extension panels of the second retractor body such that a distance between the main panel of the first retractor body and the main panel of the second retractor body is adjustable by a plurality of predetermined increments.

In some embodiments, the extension panels of the first retractor body may be in registration with the respective extension panels of the second retractor body when the first and second retractor bodies are transitioned from a contracted configuration to an expanded configuration. In some embodiments, each of the first and second retractor bodies may be transitionable to have a substantially U-shaped profile. In some embodiments, each of the main panels may include a sleeve defining a bore dimensioned to receive a fixation pin. In some embodiments, each of the main panels may include a base portion and an extension portion extending proximally from the base portion, the extension portion being more flexible than the base portion. In some embodiments, each extension panel may include a connecting portion and a retracting portion extending proximally from the connecting portion, the connecting portion connected to the base portion of the main panel by a living hinge. In some embodiments, each of the main panels may include a concave surface, the sleeve extending from the concave surface.

In another aspect, the present disclosure relates to a retractor system. In one embodiment, the system includes a fixation pin, an insertion instrument and a retractor body. The insertion instrument includes a receiving body defining a cavity therein and a handle extending from the receiving body. The retractor body includes a main panel, a first plurality of extension panels that extend from a first side of the main panel and a second plurality of extension panels that extend from a second side of the main panel. The main panel includes a sleeve configured to secure the fixation pin thereto. The retractor body is transitionable between a first configuration in which the main panel and the first and second plurality of extension panels are in a superposed relation and the retractor body is receivable in the cavity of the receiving body of the insertion instrument, and a second configuration in which the first and second plurality of extension panels are both oriented transverse relative to the main panel such that the first and second plurality of extension panels oppose each other.

In some embodiments, the main panel and the first and second plurality of extension panels may form a substantially U-shaped profile in the second configuration. In some embodiments, the main panel may include a base portion and an extension portion that is more flexible than the base portion. In some embodiments, the extension portion of the main panel may extend along a length of the main panel. In some embodiments, the extension portion of the main panel is formed of a resilient material. In some embodiments, the retractor body may include living hinge portions interconnecting the main panel and the respective first and second plurality of extension panels. In some embodiments, the first or second extension panels may be connected by living hinge portions. In some embodiments, the first and second plurality of extension panels may define a plurality of bores. In some embodiments, the retractor body in the first configuration may have a uniform width. In some embodiments, the main panel may include an arcuate surface.

In one aspect, the present disclosure relates to a method of creating access to a spinal column. In one embodiment, the method includes: inserting a first retractor body into a patient and securing the first retractor body to a first vertebra of the patient with a first fixation pin, the first retractor body including a main panel and extension panels extending from opposite sides of the main panel; inserting a second retractor body into a patient and securing the second retractor body to the first vertebra or a second vertebra with a second fixation pin, the second retractor body including a main panel and extension panels extending from opposite sides of the main panel; converting the first retractor body from an initial flat or folded configuration to a U-shaped configuration; converting the second retractor body from an initial flat or folded configuration to a U-shaped configuration such that extension panels of the second retractor body overlap with extension panels of the first retractor body; and accessing a space between the first fixation pin and the second fixation pin to perform a surgical procedure.

In some embodiments, the method also includes drilling a hole into two adjacent vertebrae each sized to receive one of the first and second fixation pins.

BRIEF DESCRIPTION OF THE DRAWINGS

Various embodiments of the present disclosure are described hereinbelow with reference to the drawings, wherein.

DETAILED DESCRIPTION

Figure 1:
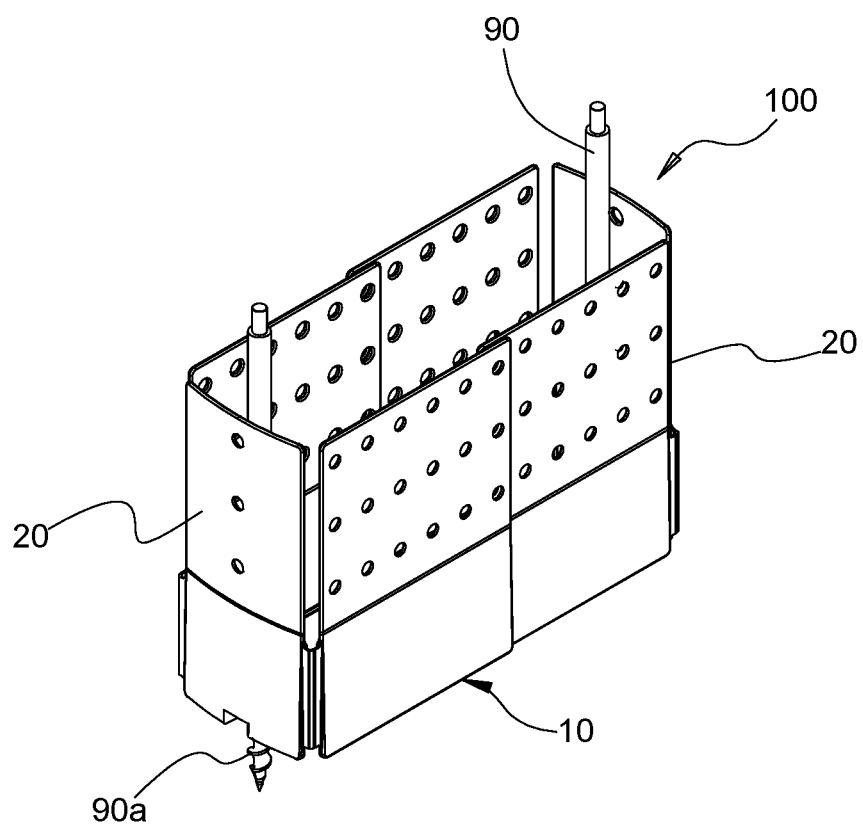
FIG. 1 is a perspective view of a retractor system in accordance with an embodiment of the present disclosure.

Embodiments of the present disclosure will now be described in detail with reference to the drawings, in which like reference numerals designate like elements in each of the several views. As used herein, the term "distal," as is conventional, will refer to that portion of the instrument, apparatus, device or component thereof which is farther from the user (e.g., clinician) while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front.

Figure 2:
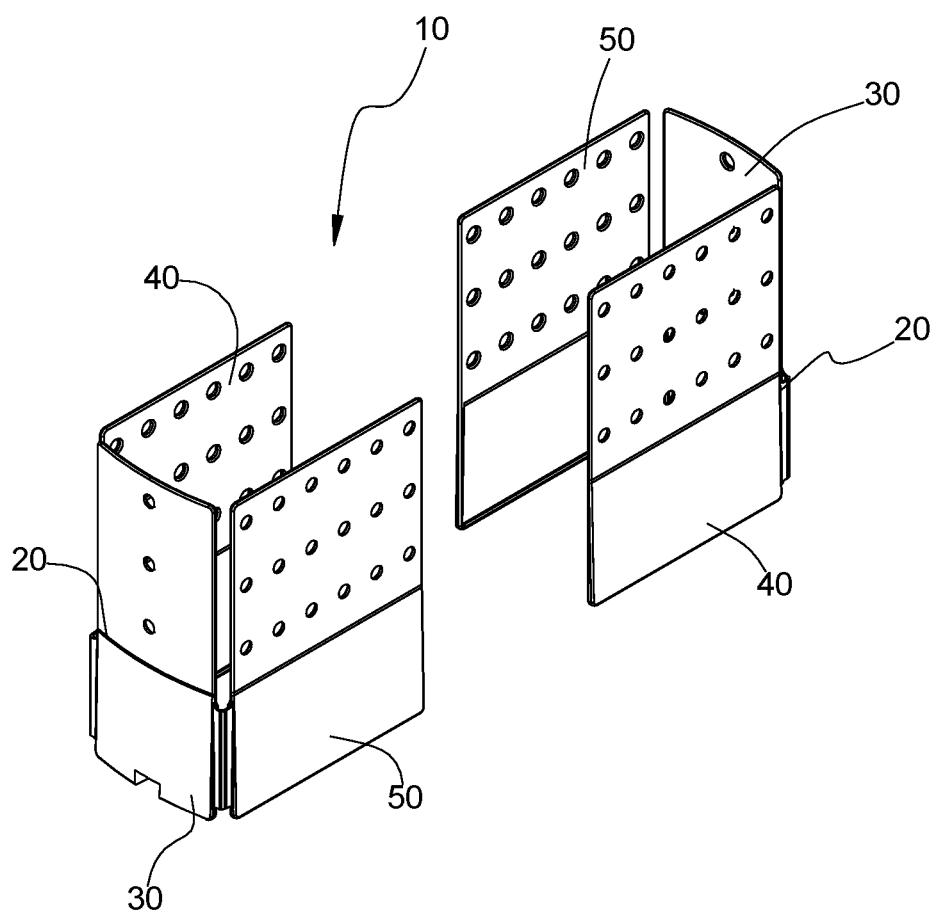
FIG. 2 is a perspective view of a retractor assembly of the retractor system of FIG. 1.
Figure 3:
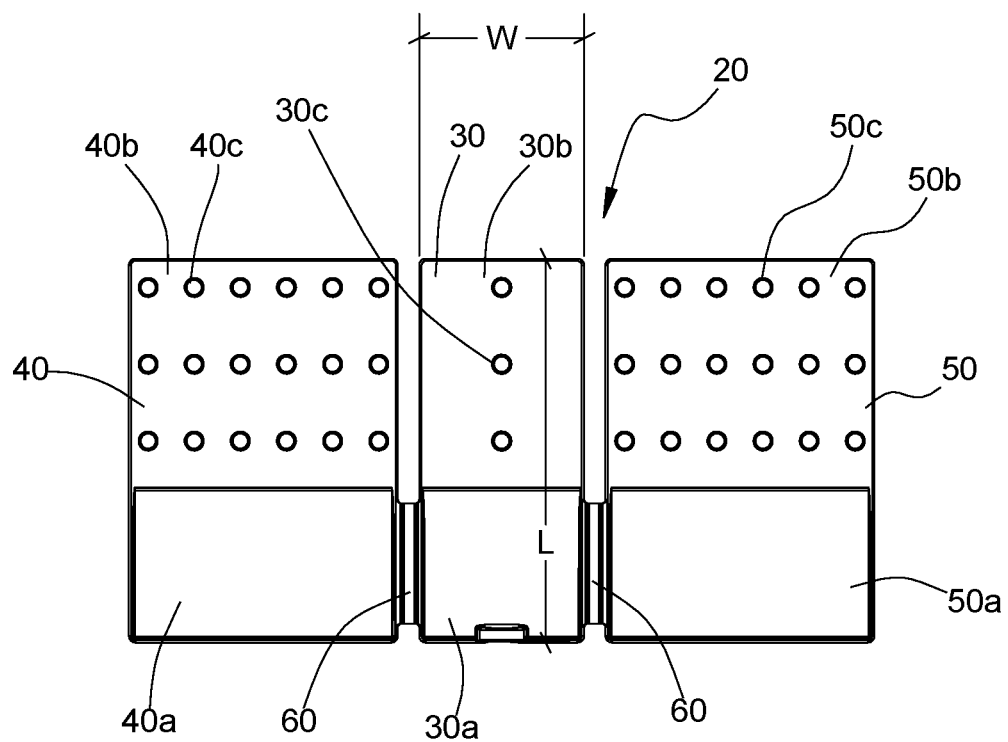
FIG. 3 is a side view of a retractor body of the retractor assembly of FIG. 2 illustrating the retractor body in a substantially flat configuration.

In one aspect, the present disclosure relates to a retractor system. With reference to FIGS. 1-3, an embodiment of the present disclosure is shown generally as a retractor system 100 configured and adapted for a minimally invasive surgical procedure to access, for example, the cervical vertebrae. However, it is envisioned that the retractor system 100 may be utilized in other procedures such as, for example, anterior lumbar interbody fusion (ALIF) and discectomy procedures for retracting soft tissue. The retractor system 100 includes a retractor assembly 10 and a pair of fixation pins 90. The retractor assembly 10 includes a pair of retractor bodies 20. Each fixation pin 90 has a threaded distal portion 90a for engaging a bone or a vertebral body, and a flange portion (not shown) having a larger diameter than the threaded distal portion 90a. The fixation pins 90 are configured to be coupled with the respective retractor bodies 20 to securely fix the retractor bodies 20 to the respective vertebral bodies.

Figure 4:
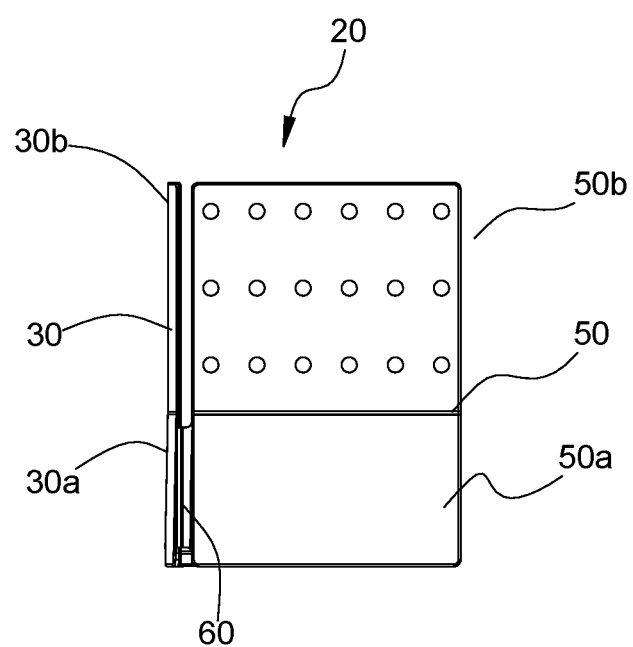
FIG. 4 is a side view of the retractor body of FIG. 1 illustrating a bent configuration.

With reference to FIGS. 2-4, each retractor body 20 includes a main panel 30 and extension panels 40, 50 interconnected by the main panel 30. In particular, the main panel 30 is connected to the extension panels 40, 50 by respective hinges 60. Each hinge 60 may be a living hinge. The hinges 60 are flexible to enable transition of the retractor body 20 between a substantially flat, or first configuration (FIG. 3) and a bent, or second configuration having a substantially U-shaped profile (FIG. 2) such that the extension panels 40, 50 oppose each other. It should be appreciated that in the first configuration, the retractor body may be in a fully extended flat configuration, such as that shown in FIGS. 3 and 6, or it may be flat with one or more extension panels folded over the main panel. Turning to the details of the hinges, the hinges 60 may have a smaller thickness than the main panel 30 and the extension panels 40, 50 to facilitate transition of the retractor body 20 between the substantially flat configuration and the bent configuration. In particular, each hinge 60 may be formed of a high-impact resistant homopolymer polypropylene material that is a clear amorphous thermoplastic. Such material enables customization in the operating room by surgical scissors, and is sufficiently malleable to fold and unfold creating a living hinge. It is also contemplated that the main panel 30, the extension panels 40, 50, and the hinges 60 may be formed monolithically. In particular, the entire retractor body 20 may be formed of polypropylene (PP).

With particular reference to FIGS. 3 and 4, the main panel 30 is partitioned into a base portion 30a and an extension portion 30b extending proximally from the base portion 30a. In particular, the base portion 30a may be more rigid than the extension portion 30b to provide structural rigidity on a side of the retractor body 20 that includes the base portion 30a as it is advanced into the patient first and engages the vertebral body. The extension portion 30b may be less rigid than the base portion 30a such that the extension portion 30b provides decreased tension on the soft tissue during retraction, thereby reducing trauma to tissue and instances of, e.g., dysphagia and neural praxia (transient recurrent laryngeal nerve palsy).

With continued reference to FIGS. 3 and 4, the extension panels 40, 50 include respective base portions 40a, 50a and respective extension portions 40b, 50b extending proximally from the respective base portions 40a, 50a. As discussed with respect to the main panel 30, the base portions 40a, 50a may have greater rigidity than the extension portions 40b, 50b. Alternatively the base portions 40a, 50a may be reinforced or may have a larger thickness than the extension portions 40b, 50b such that the base portions 40a, 50a engaging the vertebral bodies provide the structural rigidity when engaging vertebral bodies. The extension portions 40b, 50b have a smaller thickness than the base portions 40a, 50a such that the extension portions 40b, 50b provide decreased tension on the soft tissue during retraction, thereby reducing trauma to tissue and reducing instances of, e.g., dysphagia and neural praxia. In order to further reduce the tension on the soft tissue by the extension portions 40b, 50b, the hinges 60 interconnect the base portion 30a of the main panel 30 and the respective base portions 40a, 50a of the extension panels 40, 50. In addition, each extension portion 30b, 40b, 50b may define a plurality of bores 30c, 40c, 50c to improve flexibility of the extension portions 30b, 40b, 50b. In particular, the bores 30c, 40c, 50c may be uniformly dimensioned to operatively engage with arms 70 (FIG. 9), as will be discussed hereinbelow. In addition, a common spreader such as, e.g., Gelpi retractor, may be utilized to spread the retractor assembly 10. Reference may be made to International Patent Application Publication No. WO 2008/039247, the entire contents of which are incorporated herein by reference, for a detailed description of one example of the construction and operation of Gelpi retractor. In some examples, arms 70 are configured to hold opposing retractor bodies 20 so that a distance between main panels 30 is preserved. In some examples, a Gelpi retractor in position in the system preserves a separation distance between opposing extension panels.

Figure 5:
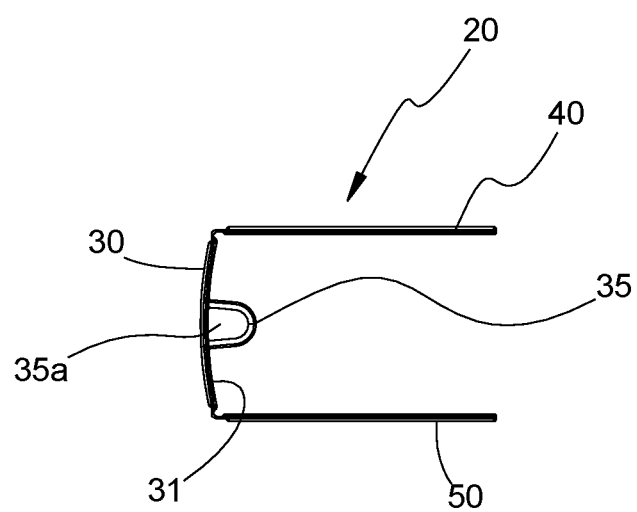
FIG. 5 is a top view of the retractor body of FIG. 4 illustrating the bent configuration.
Figure 6:
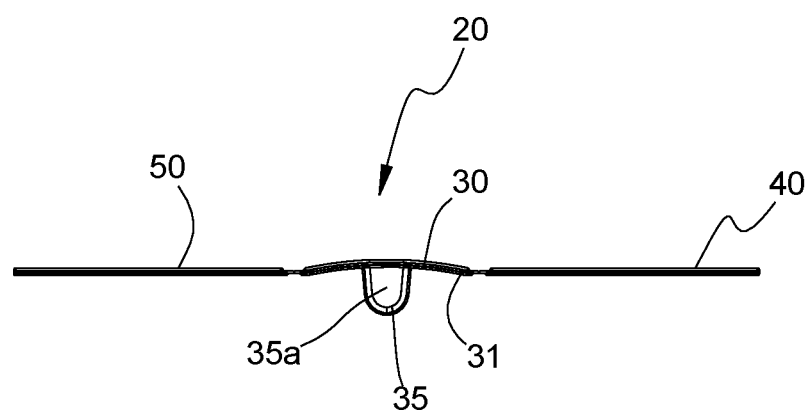
FIG. 6 is a top view of the retractor body of FIG. 3 illustrating the substantially flat configuration.

With reference now to FIGS. 5 and 6, each retractor body 20 may be manipulated or bent to define a substantially U-shape. In particular, the main panel 30 has a slight curvature to facilitate manipulation of the extension panels 40, 50 towards each other to form the substantially U-shape. In addition, the main panel 30 includes a sleeve 35 defining a bore 35a therethrough. In particular, the sleeve 35 may extend from a concave surface 31 of the main panel 30. The bore 35a is configured to receive the fixation pin 90 (FIG. 1) therethrough in order to securely fix the retractor body 20 to a vertebral body. In particular, when the threaded distal portion 90a is threadably received in the vertebral body, the flange portion (not shown) of the fixation pin 90 is pressed against the sleeve 35, which, in turn, presses the sleeve 35 against the vertebral body to enhance securement of the retractor body 20 to the vertebral body. The extension panels 40, 50 oppose each other in the bent configuration and may be substantially parallel to each other. The sleeve 35 may extend along a length of the main panel 30. In particular, the sleeve 35 may extend a length along the base portion 30a (FIG. 3) of the main panel 30.

Figure 7:
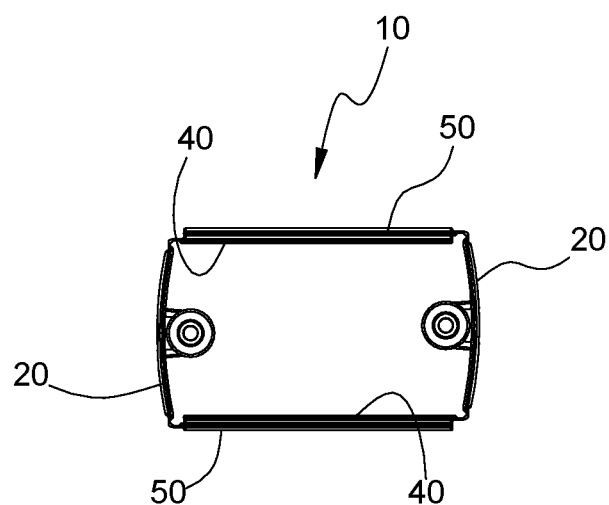
FIG. 7 is a top view of the retractor assembly of FIG. 2 illustrating an assembled configuration.
Figure 8:
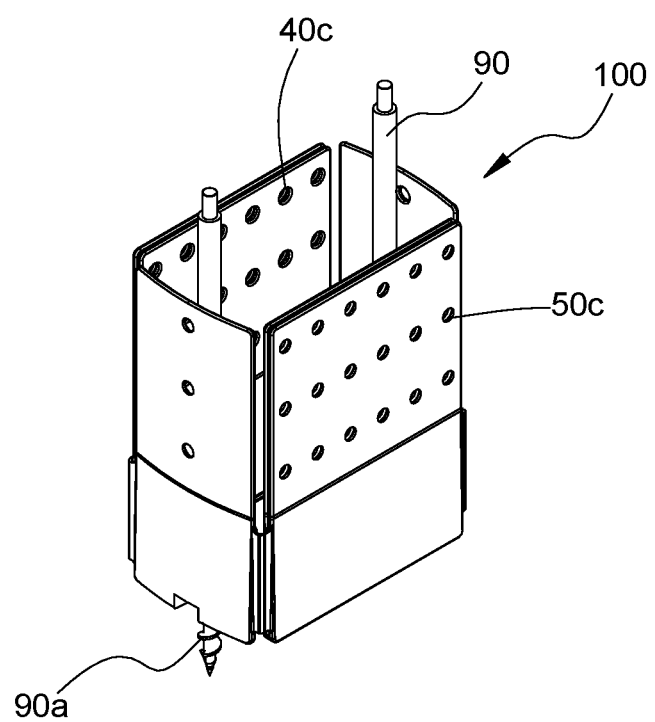
FIG. 8 is a perspective view of the retractor system of FIG. 7 illustrating a contracted configuration.

With reference now to FIGS. 7 and 8, when the retractor bodies 20 are assembled to form the retractor assembly 10, e.g., each retractor body 20 has the substantially U-shaped profile, the extension panels 40, 50 of the retractor bodies 20 overlap one another. To secure the position of the extension panels of each the retractor body, a locking mechanism may be used. For example, locking arms 70 (FIG. 9) may be utilized to lock the relative position of the extension panels 40, 50 by inserting pegs 72, 74 of the locking arm 70 through the overlapping bores 40c, 50c of the overlapping extension portions 40b, 50b of the extension panels 40, 50. In this manner, the clinician may selectively lock, i.e., fix the retractor bodies with respect to one another, and, at the same time, maintain the distance between the fixation pins 90.

With reference to FIGS. 10-14, another embodiment of the present disclosure is shown generally as a retractor system 200 configured and adapted for a minimally invasive surgical procedure to access vertebrae. For example, the retractor system 200 may be used in a discectomy for retracting soft tissue. The retractor system 200 includes a retractor assembly 210 and an insertion instrument 300 configured to facilitate placement of the retractor assembly 210 in a surgical site. As discussed hereinabove with respect to the retractor system 100, the retractor assembly 210 may include a pair of retractor bodies 220. Portions of the retractor body 220 identical to the portions of the retractor body 20 (FIG. 1) will not be described in order to avoid obscuring the present disclosure in unnecessary detail.

Figure 12:
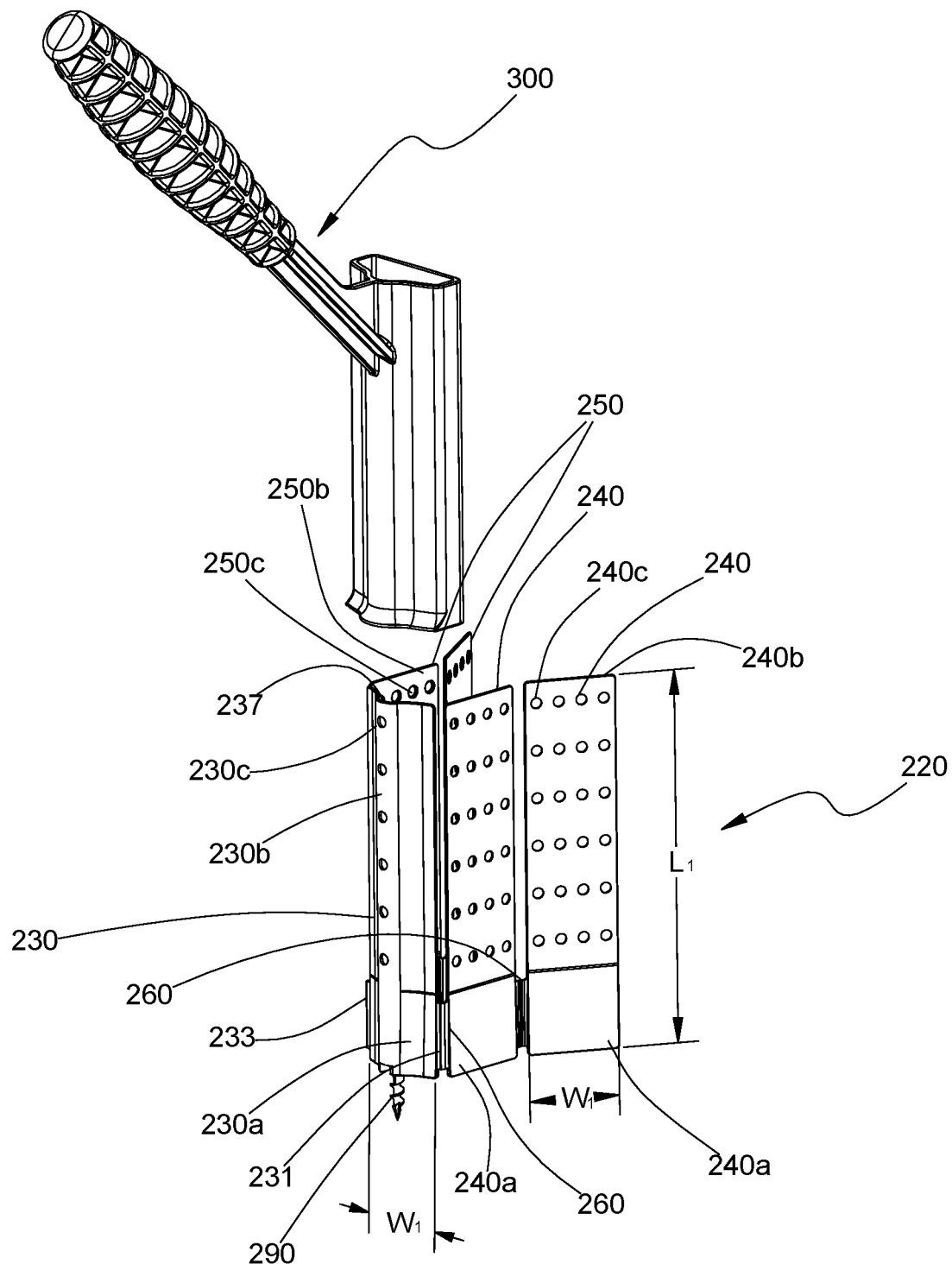
FIG. 12 is a perspective view of the retractor system of FIG. 10, illustrating the retractor body removed from the insertion instrument.
Figure 13:
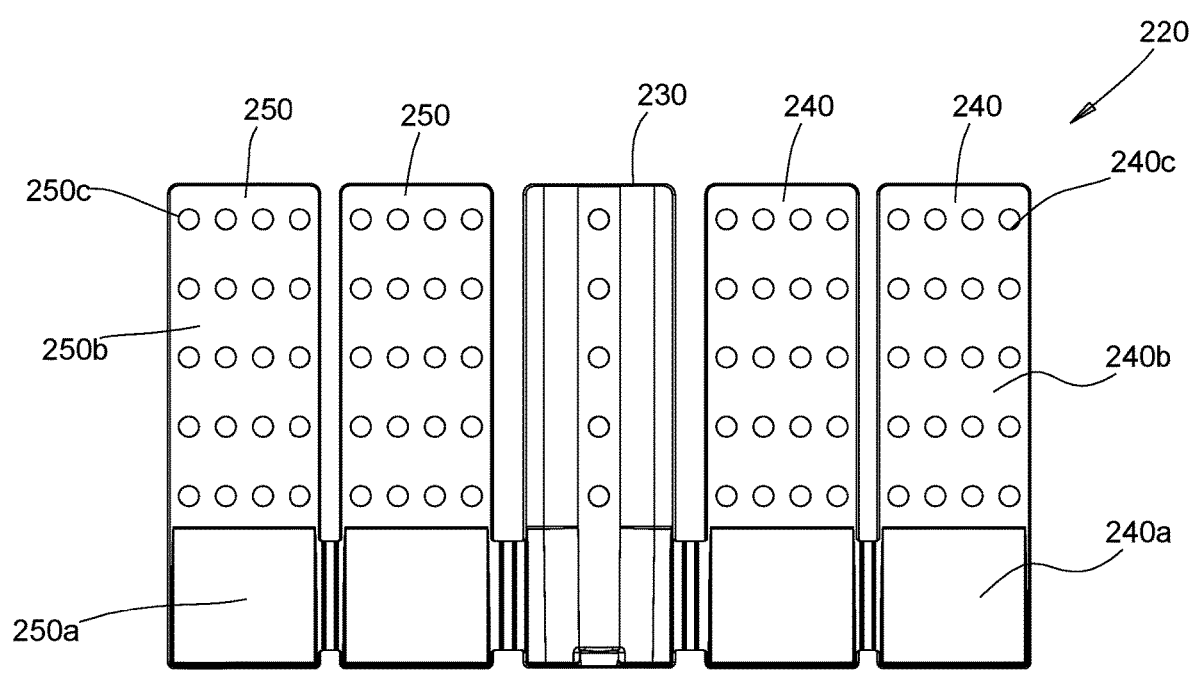
FIGS. 13-14 are side and top views, respectively, of the retractor system of FIG. 10.
Figure 14:
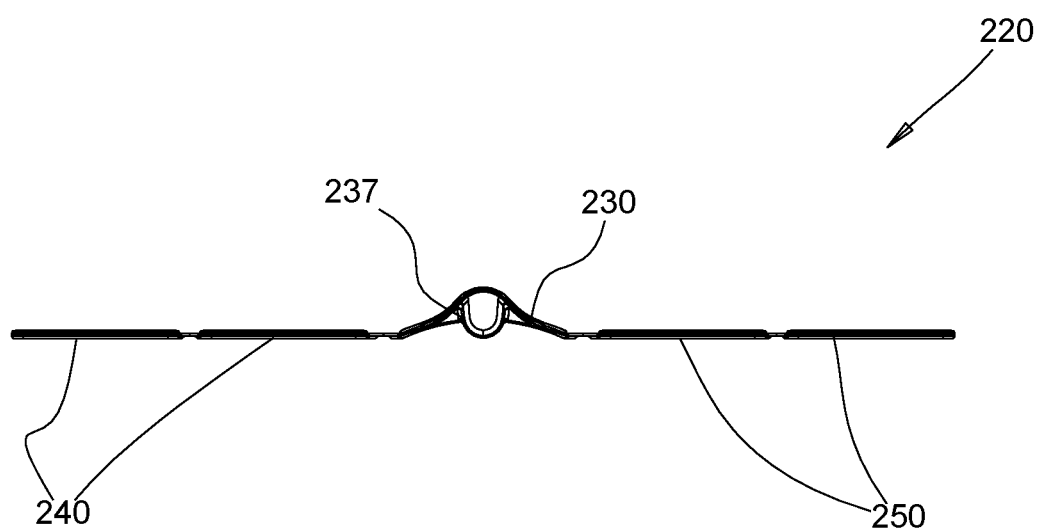

With particular reference to FIG. 12, the retractor body 220 may be used with the fixation pin 90 (FIG. 1) in order to secure the retractor body 220 to a vertebral body, as discussed hereinabove. The retractor body 220 includes a main panel 230 and extension panels 240, 250. In particular, a plurality of extension panels 240 extends laterally from a first side 231 of the main panel 230, and a plurality of extension panels 250 extends laterally from a second side 233 of the main panel 230. The plurality of extension panels 240, 250 and the main panel 230 are connected by respective hinges 260. In addition, the extension panels 240 are connected to each other by respective hinges 260, and the extension panels 250 are also connected to each other by respective hinges 260.

Each hinge 260 may be a living hinge. The hinges 260 are flexible to enable transition of the retractor body 220 between a folded, or first configuration (FIG. 10) and a bent, or second configuration forming a substantially U-shaped profile (FIG. 12) such that the extension panels 240, 250 oppose each other. For example, the hinges 260 may have a smaller thickness than the main panel 230 and the extension panels 240, 250 to facilitate transition of the retractor body 220 between the folded configuration and the bent configuration.

In particular, each hinge 260 may be formed of a high-impact resistant polypropylene or homopolymer polypropylene material that is a clear amorphous thermoplastic. Such material further enables customization in the operating room by surgical scissors, and is sufficiently malleable to fold and unfold creating a living hinge. Under such a configuration, the clinician may customize the retractor body 220 to a surgical procedure being performed by removing the extension panels 240, 250 by, e.g., cutting through a hinge 260. In this manner, the clinician may customize the retractor body 220 for use with multi-level vertebral bodies. It is also contemplated that the main panel 230, the extension panels 240, 250, and the hinges 260 may be formed monolithically. In particular, the entire retractor body 220 may be formed of polypropylene.

In some embodiments, the hinge may be biased in the open position. In this manner, the retractor body with biased hinges will naturally have a U-shaped profile or another profile with parallel extension panels, and may be foldable to fit within an instrument 300.

The main panel 230 is partitioned into a base portion 230a and an extension portion 230b secured with the base portion 230a. The main panel 230 includes a length L1 and a width W1. At least a portion of the extension portion 230b extends along the length L1. In particular, a portion of the extension portion 230b extends along the entire length L1 of the main panel 230 and has an arcuate profile defining a concave surface 237 configured to slidably receive a fixation pin 290 therein, as shown in phantom in FIG. 12. A proximal portion (not shown) of the concave surface 237 includes a sleeve (not shown) defining a bore (not shown) configured to receive the fixation pin 290 therethrough in order to securely fix the retractor body 220 to a vertebral body, as discussed with respect to the sleeve 35 (FIG. 5). The base portion 230a and the extension portion 230b of the main panel 230 have a uniform width W1. As shown in FIG. 12, the main panel 230 has a generally V-shaped cross-section. It should be appreciated, however, that in alternative configurations, this shape along with the instrument 300 may be varied to have another shape that also provides for slidable insertion of the retractor body into the instrument.

The base portion 230a may be more rigid than the extension portion 230b such that the base portion 230a engaging the vertebral body provides the structural rigidity when engaging vertebral bodies. The extension portion 230b may be less rigid than the base portion 230a such that the extension portion 230b provides decreased tension on the soft tissue during retraction, thereby reducing trauma to tissue and instances of, e.g., dysphagia and neural praxia (transient recurrent laryngeal nerve palsy).

Figure 9:
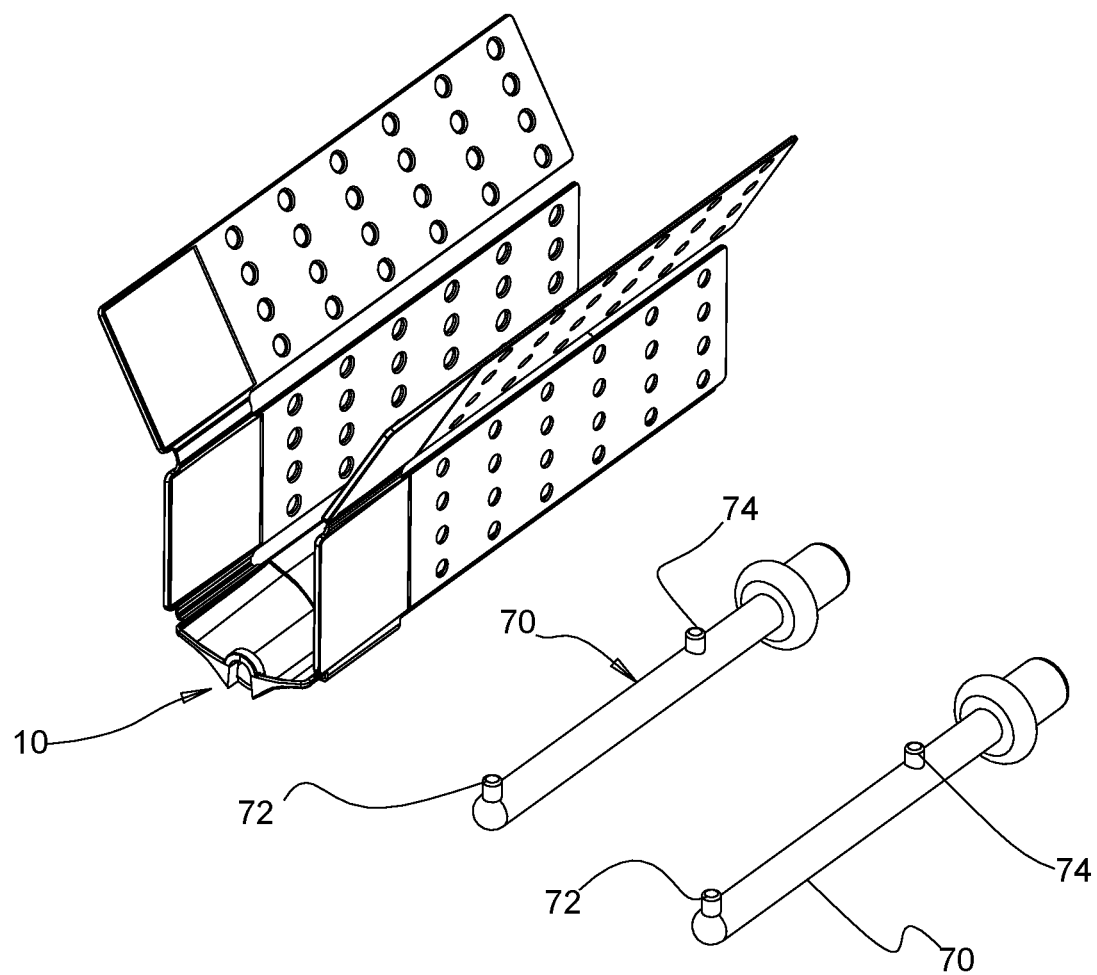
FIG. 9 is a perspective view of the retractor assembly of FIG. 1 and a pair of locking arms for use with the retractor assembly.

The extension panels 240, 250 include respective base portions 240a (base portion of the extension panel 250 not shown) and respective extension portions 240b, 250b extending proximally from the respective base portions 240a. Each of the extension panels 240, 250 has a uniform width W1 identical to the width W1 of the main panel 230. As discussed with respect to the main panel 230, the base portions 240a of the extension panels 240, 250 may have greater rigidity than the respective extension portions 240b, 250b. Alternatively the base portions 240a of the extension panels 240, 250 may have a larger thickness than the extension portions 240b, 250b such that the base portions 240a of the extension panels 240, 250 engaging the vertebral bodies provide the structural rigidity when engaging vertebral bodies. The extension portions 240b, 250b may be less rigid than the respective base portions 240a such that the extension portions 240b, 250b provide decreased tension on the soft tissue during retraction, thereby reducing trauma to tissue and reducing instances of, e.g., dysphagia and neural praxia. In addition, each extension portion 230b, 240b, 250b may define a respective plurality of bores 230c, 240c, 250c to improve flexibility of the extension portions 230b, 240b, 250b. Additionally, the bores 230c, 240c, 250c may be uniformly dimensioned to operatively engage the locking arms 70 (FIG. 9).

The retractor body 220 may be manipulated or bent between the folded configuration (FIG. 10) and the bent configuration, in which, the retractor body 220 forms a substantially U-shape (FIG. 12). In the folded configuration, the main panel 230 and the extension panels 240, 250 having the same width W1 are in a superposed relation. In particular, the concave surface 237 of the main panel 230 is spaced part from the extension panels 240, 250 such that the fixation pin 90 (FIG. 1) may be inserted through the concave surface 237 when the retractor body 220 is in the folded configuration. In this manner, the retractor body 220 may be secured to a vertebral body by the fixation pin 90 while the retractor body 220 is folded and disposed in the insertion instrument 300, as described elsewhere in the present disclosure.

In the bent configuration, the extension panels 240, 250 oppose each other and may be substantially parallel to each other. When a pair of retractor bodies 220 is utilized, each retractor body 220 may form the substantially U-shaped profile such that the extension panels 240, 250 of the retractor bodies 220 overlap to define a working space for the clinician to access the vertebral bodies. While the retractor bodies are in the U-shaped configuration, the locking arms 70 (FIG. 9) may be utilized to lock the relative position of the extension panels 240, 250 by inserting pegs 72, 74 of the locking arm 70 through any selection of the overlapping bores 240c, 250c of the overlapping extension portions 240b, 250b of the extension panels 240, 250. In this manner, the clinician may selectively lock, i.e., fix the retractor bodies at a desired spacing, e.g., in superior-inferior axis along the spine, and maintain the distance between the fixation pins 90 by holding their position with respect to each other.

Figure 10:
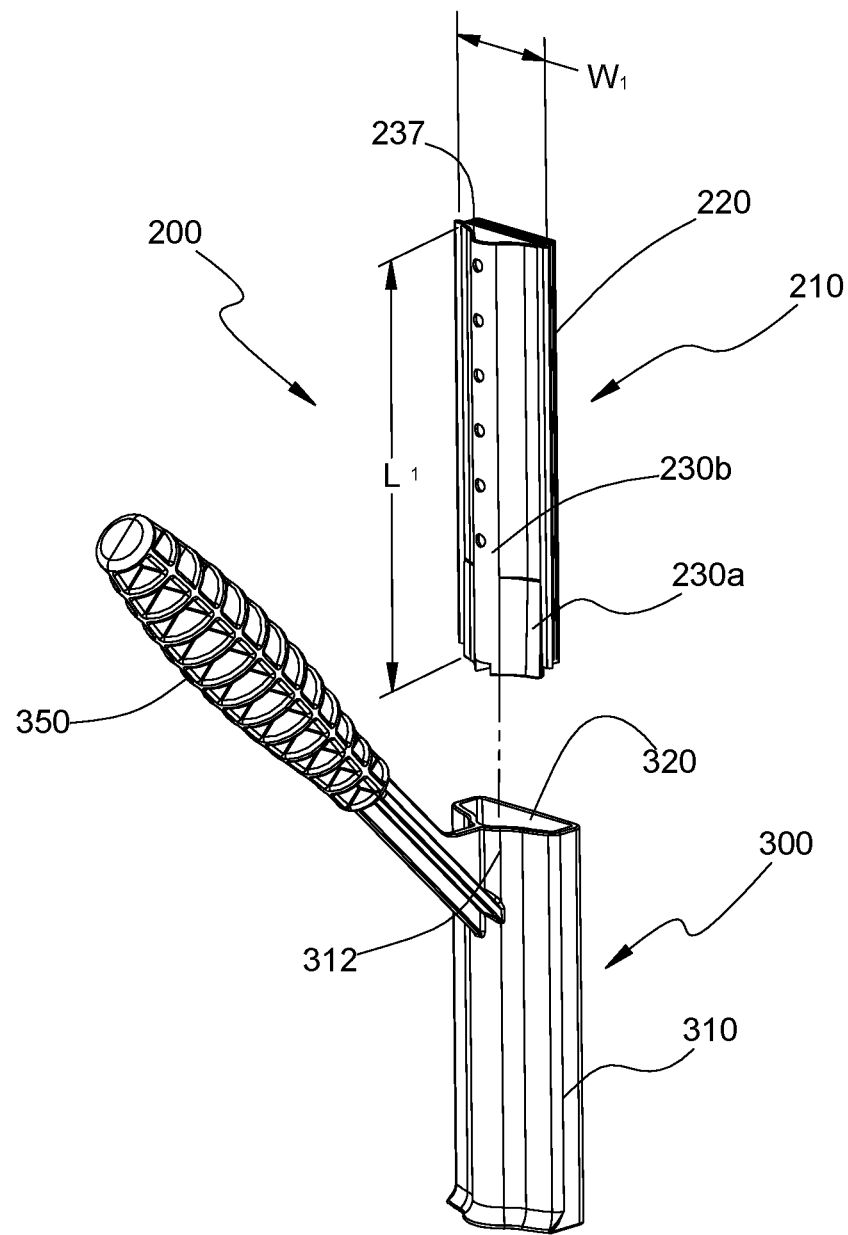
FIG. 10 is a perspective view of a retractor system in accordance with another embodiment of the present disclosure.

With brief reference to FIG. 10, the insertion instrument 300 includes a receiving body 310 defining a cavity 320 dimensioned to receive the retractor body 220 in the folded configuration. In particular, the cavity 320 includes an arcuate portion 312 having a shape complementary to a shape of the arcuate profile of the main panel 230 of the retractor body 220. Under such a configuration, the retractor body 220 in the folded configuration may be slidably received in the receiving body 310. The insertion instrument 300 further includes a handle 350 transversely extending from the receiving body 310 in order to facilitate placement of the retractor body 220 in the surgical site. Retractor body 220 is advantageous in that even with multiple extension panels, each extension panel may be folded over the main panel to convert the retractor body 220 to a flat configuration, thereby allowing for its compact insertion into instrument 300. Thus, the retractor body is configured for insertion into a patient in a compact manner, yet still creates a large retraction structure when expanded.

Figure 15:
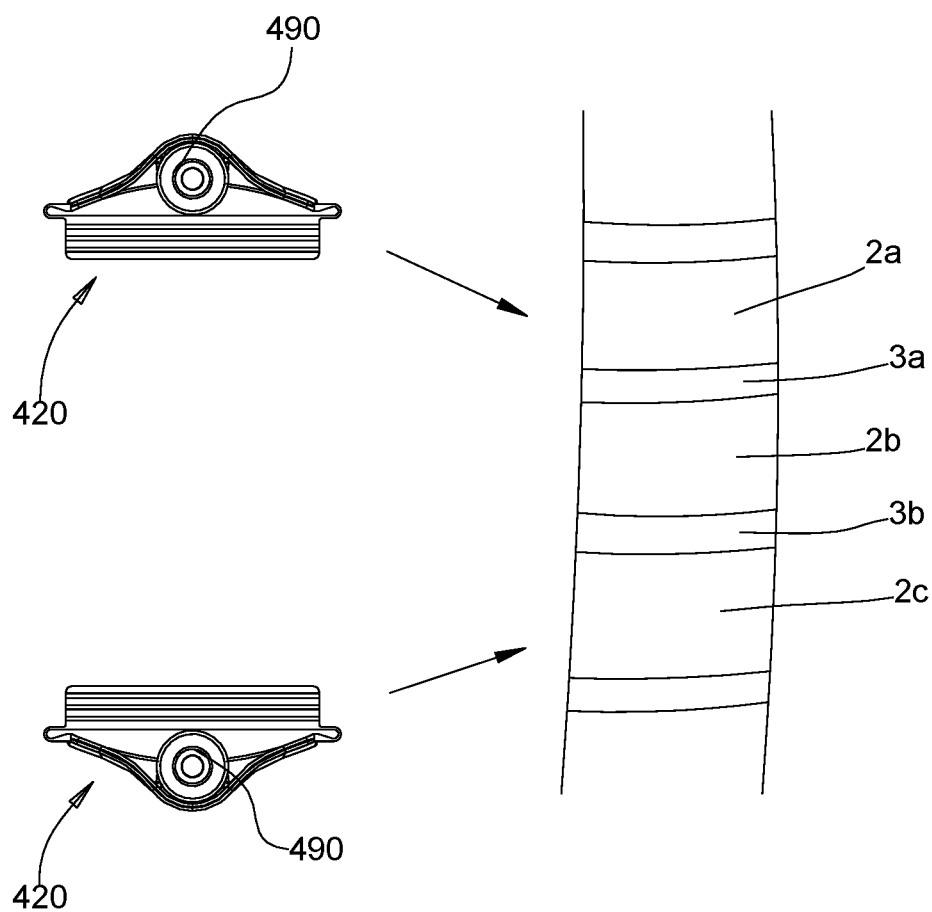
FIGS. 15-18 are top views of steps in a method of using the retractor system according to one embodiment of the disclosure.

In yet another embodiment, a retractor body of a retractor system may be as shown in FIG. 15. References to the 400 series of numbers refer to like elements in the 100 series of numbers, unless otherwise noted. Retractor body 420 includes a main panel 430 with a curved central region that accommodates a sleeve (not shown) so that a pin 490 is insertable while still leaving room for extension panels 440, 450 to be folded over main panel 430 in a first configuration, again shown in FIG. 15. Elsewhere in the disclosure, this embodiment is referenced to describe one example of a method of using the retractor system.

The retractor system may be varied in many ways. For example, when the retractor bodies are assembled to form the retractor assembly, each retractor body may have a profile that is different from a U-shape. For instance, each extension panel on a retractor body may be in parallel and at the same acute angle relative to an axis through the main panel when configured for overlapping with a complementary retractor body. In some examples, the angle of the parallel extension panels may be 70-110 degrees relative to the axis through the main panel. In some examples, the angle of the parallel extension panels may be 80-100 degrees relative to the axis through the main panel. In some examples, the angle of the parallel extension panels may be 85-95 degrees relative to the axis. Because the extension panels on each retractor body are all in parallel and at the same angle relative to axes through the parallel main panels, such extension panels may be overlapping when one retractor body is slid over the other.

Turning to the size of the retractor bodies, in some examples, a size of a first retractor body may be different from a size of a second retractor body. For instance, the first retractor body may be sized to fit within the second retractor body when the retractor bodies are combined in an overlapping configuration. Further, the first retractor body may have extension panels that are each the same width, but such width being lesser or greater than a width of the extension panels on the second retractor body. The reference characters W and L shown in FIG. 3 denote the width and length of the panels, respectively. These variations may be used to alter the maximum and minimum size of the enclosure between the retractor bodies and the range of sizes in between the maximum and minimum size, i.e., the range of possible overlap for a planned surgery.

Turning to the details of the panels in each retractor body, in some examples, a retractor body may have a main panel with an extension panel on each side of the main panel where the respective extension panels are different sizes. For instance, one extension panel may extend further from the main panel than the other. In some examples, one or more extension panels may have a width greater than a width of the main panel. In other examples, one or more extension panels have a width less than a width of the main panel. To optimize folding of the extension panels over the main panel for use in a first folded configuration, the width W of each extension panel should be the same or less than a width W of the main panel. The above principles may also be applied to the length of the panels, such that one panel may have a different length than another panel on the same retractor body. In still other examples, a thickness of the main panel may be different from a thickness of the extension panels or any one panel may have a thickness different from one or more other panels on the retractor body.

Turning to the properties of the panels that improve flexibility, the bores may vary from the depicted embodiments and in some examples may be substituted with other elements. For example, where the panels of the retractor body have bores, the bores may have a non-circular shape and may have any number of patterns. For example, the bores may be aligned in parallel rows that are equally spaced from one another. In other examples, the bores may be aligned in rows that are at different spacing from one another. In further examples, each row of bores may have a unique pattern of bores or a unique number of bores. In other examples, the bores may not be arranged specifically in rows. In the above examples, it is desirable to ensure that the bores of an extension panel on a first retractor body align with the bores of an extension panel on a second retractor body that is configured to overlap with the extension panel on the first retractor body so that a locking arm or other similar element may be placed through a pair of bores, two pairs of bores, or more, to fix the bodies with respect to one another. The wide variety of possible patterns for the bores may dictate the possible predetermined increments available to a clinician to create portals of different sizes via selective fixation of the retractor bodies to one another. In other examples, the panels may have flexible properties through variations in thickness, through the use of varying materials over the surface area or through the use of a single material with desirable flexural properties. In these examples, a separate locking element other than a pin may be used to secure the retractor bodies to one another. For instance, a clip attachable to an insertion instrument may be used to lock the retractor bodies to one another.

Turning to the hinge of the retractor bodies, as noted elsewhere in the disclosure, the hinge may be biased to have an angled profile so that an extension panel is angled relative to a main panel in its natural state. Elastic materials may be used. The hinge may be configured so that the panels may be made flat with respect to one another, e.g., folded, by force, and may return to a U-shape or other closed position upon removal of the applied force. In other examples, the hinge may be a separate element combined with the panels of the retractor body. In some examples, the hinge may be a different material than the panels.

Turning to the structure configured to allow passage of a fixation pin therethrough, in some examples, the sleeve shape may be varied to have any desired profile. These variations may be used to complement a shape of fixation pin to be used. The sleeve may be integral with the remainder of the retractor body or may be an attachable element. The sleeve may extend over a portion of a panel height or the full height. In some examples, the sleeve is fully enclosed. In other examples, the sleeve is a C-clip with an open face and is configured so that a fixation pin may be slid into the C-clip while also prevented from movement in directions other than an axial direction to keep the pin in the clip during use. In this manner, a pin is prevented from becoming dislodged in a direction transverse from an axis through the clip. Other structures configured for slidable engagement are also contemplated.

The mechanism configured to lock each retractor body of the system to the other may also be varied. In some examples, the locking arms may include a single peg. In other examples, the locking arms may have a non-circular cross-section to complement a non-circular cross section of the bores on the retractor bodies. The system may include any number of locking arms. In other examples, fixation against movement between respective retractor bodies is accomplished using an alternative to locking arm 70. For example, a clip as referenced above may be used. The clip may be biased to a closed position and may be used to hold the respective retractor bodies together in an overlapping position. In such examples, bores may optionally be absent from each retractor body.

For retractor bodies with more than one extension panel on at least one side of the main panel, any number of extension panels may be included. It should be appreciated that the example variations of the retractor body structure described throughout the disclosure may apply to any retractor body described herein, including as variations of the retractor body shown in FIG. 1 and in FIG. 10, for example.

In another aspect, the present disclosure relates to a method of using the retractor system. Although the methods described herein are directed to an anterior approach to the cervical region of the spine, it should be appreciated that the retractor system of the present disclosure is not limited to such applications. In use, the clinician may utilize fluoroscopy or another imaging modality to identify the correct operative level and make one or more incisions through the patient's skin using conventional instruments. The number and type of incisions (e.g. transverse or vertical) may be tailored to the procedure being performed. Once verified, the clinician prepares the vertebral bodies. For example, the clinician may optionally utilize an indicator pin. The clinician locates the center of a vertebral disc space and inserts the indicator pin (not shown) thereto. The indicator pin may serve as a center point in, e.g., a medial-lateral direction and/or in the cephalad-caudal direction.

In one embodiment, the method is performed as shown in FIGS. 15-18. Initially, optionally using the center point on the vertebrae as a guide, end points for the intended opening into the patient are identified on one or more vertebral bodies. For example, for the placement of bone plate 8 (FIG. 18), insertion locations for pins 490 are identified on vertebral bodies 2a, 2c, respectively. At this juncture, the retractor bodies are ready to be secured to a vertebra or vertebrae of the spine. To prepare each retractor body, and with reference to FIGS. 8 and 15, the first fixation pin 490 is received through the bore of the sleeve (not shown) of a first retractor body 420. A fixation pin is received in a second retractor body in the same manner, thereby preparing two retractor bodies for insertion into a patient, as shown in FIG. 15. Each retractor body is either in a folded, first configuration as shown in FIG. 15, or is adjusted to the first configuration, prior to manual insertion into the patient by a clinician. The clinician may insert each retractor body in the first configuration through tissue of the patient until the respective pin is adjacent the bone surface. Each pin is then driven, e.g., via rotation, into an identified location on a vertebral body, i.e., into vertebrae 2a, 2c, respectively. The fixation pins 490 are self-tapping in the sense that no pre-drilled hole in the bone is required to secure the pins to the bone. In a variation of this approach, standard retraction tools may be used to create a temporary passage to the spine to provide greater visibility. Each retractor body remains in the flat, i.e., in the first configuration during insertion. In a variation of this method, the pins may be inserted independently into the patient initially, with the retractor body sleeves inserted over the pins while the pins are in position secured to bone.

Figure 16:
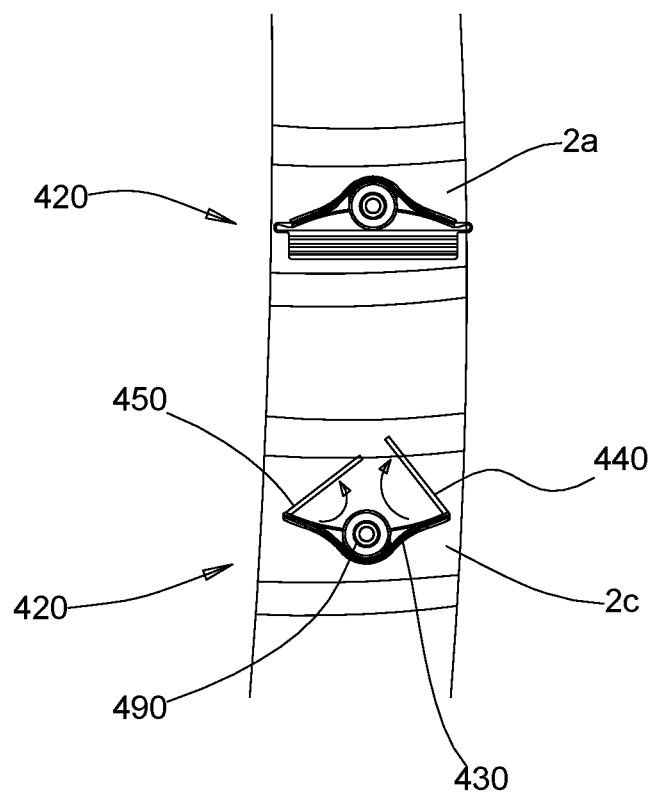
Figure 17:
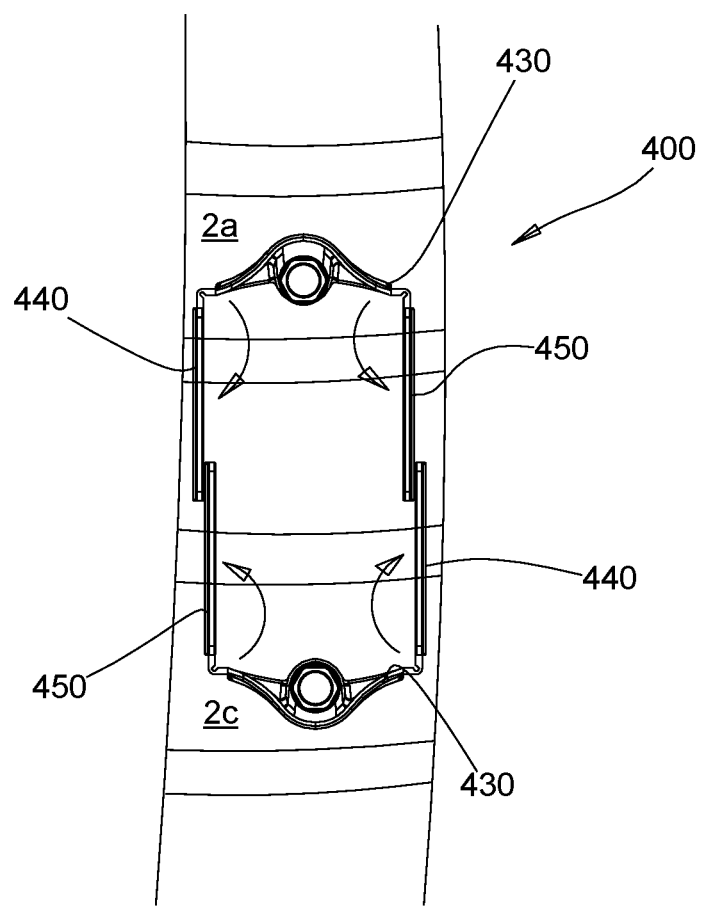

From the flat configuration shown for one of the retractor bodies in FIG. 16, the clinician may rotate the extension panels of retractor bodies 420 in, e.g., the medial-lateral direction as shown in FIG. 16, away from the respective main panel, thereby pushing tissue away from the desired surgical path, to create a portal to the target site. The extension panels are rotated until each one is approximately perpendicular to a respective main panel. When this process is completed for both of the opposing retractor bodies, opposing extension panels 440, 450 of each retractor body 420 overlap one another, as shown in FIG. 17. In this manner, the clinician retracts soft tissue by pushing it out of an enclosure formed within the panels of the retractor bodies 420.

Figure 18:
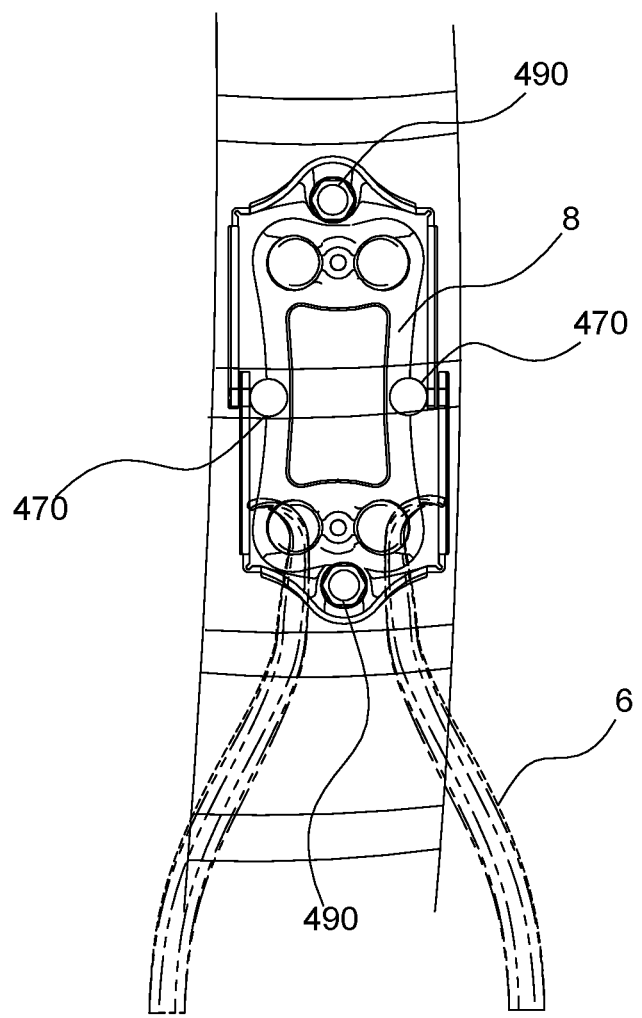

Upon positioning the extension panels 440, 450 of the retractor bodies 420, the locking arms 470 may be utilized on overlapping extension panels 440, 450 to secure the retractor bodies 420 relative to each other in a superior-inferior direction. For example, pegs (not shown) of arm 470 may be inserted into overlapping bores (not shown) of panels 440, 450. Optionally, a retractor, e.g., a Gelpi retractor, may be inserted at this time as shown in FIG. 18 to maintain a separation of the opposing pairs of extension panels in the medial-lateral direction.

With a surgical portal clear for use, a surgical procedure may commence. In FIG. 18, the cleared portal is shown sized to accommodate the insertion of a spinal, e.g., cervical bone plate 8 with sufficient space to secure it in place while tissue is retracted and held behind the panels of the retractor system. Upon completion of the surgical procedure, the retractor system may be removed from the surgical site.

In a variation on the embodiment described above and shown in FIGS. 15-18, a clinician may insert two retractor bodies 420 from an anterior approach and advance each retractor body to a surface of the spine prior to making a decision with respect to the anchorage points for the pins 490. In this manner, the clinician may insert each retractor body in the folded configuration, transition each retractor body into the expanded, e.g., U-shaped configuration, and then adjust each retractor body with respect to the other in a superior-inferior axis to obtain a desired position and size of a surgical access portal to the spine. During these adjustments, the extent to which the extension panels of opposing retractor bodies overlap may vary if the size of the volume between the main panels of the respective retractor bodies is altered. The overlap of extension panels may be adjusted in predetermined increments. The predetermined increments may be based on the spacing of the bores in the extension panels, for example. Once a desired position is reached, pins 490 for respective retractor bodies may be anchored into place in an applicable vertebra.

Figure 11:
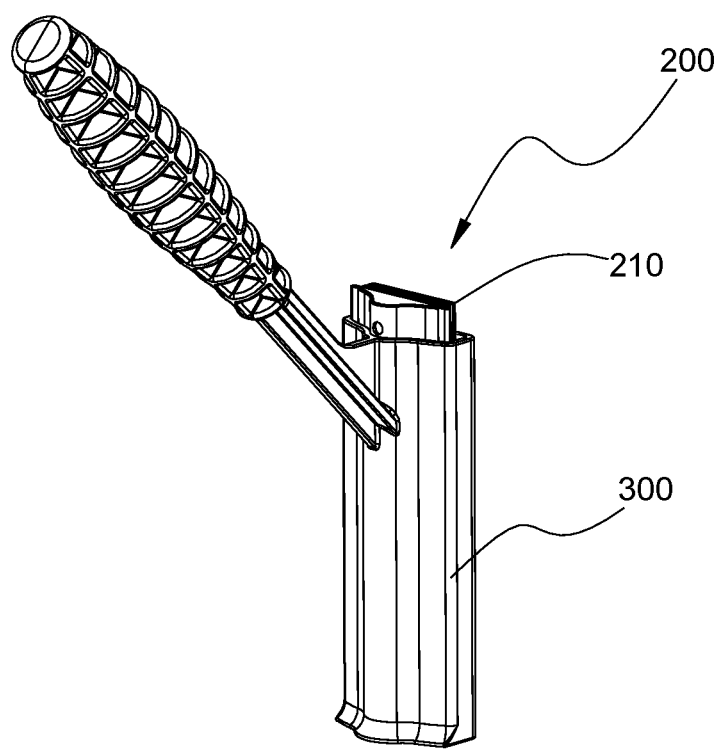
FIG. 11 is a perspective view of the retractor system of FIG. 10, illustrating insertion of a retractor body into an insertion instrument.

In another embodiment, the method may be performed with retractor system 200 shown in FIGS. 10 to 12. In the performance of the method, the clinician may utilize fluoroscopy or another imaging modality to identify the correct operative level and make one or more incisions through the patient's skin using conventional instruments. The number and type of incisions (e.g. transverse or vertical) may be tailored to the procedure being performed. Once verified, the clinician prepares the vertebral bodies. For example, the clinician may optionally utilize an indicator pin. The clinician locates the center of a vertebral disc space and inserts the indicator pin (not shown) thereto. The indicator pin may serve as a center point in, e.g., a medial-lateral direction and/or in the cephalad-caudal direction.

As can be appreciated with reference to FIG. 10, the retractor body 220 is initially converted into the flat, folded configuration, i.e., the first configuration. Thereafter, the retractor body 220 is slidably received into the cavity 320 of the receiving body 310 of the insertion instrument 300, as shown in FIG. 11. At this time, the retractor body 220 may be advanced toward the desired surgical site so that it is adjacent the surgical site. The fixation pin 90 (FIG. 1) may be utilized to secure the retractor body 220 to a desired vertebral body while the retractor body 220 is being held by the insertion instrument 300. Alternatively, the insertion instrument 300 may be removed prior to securing the retractor body 220 to the vertebral body via the pin. Concurrently or subsequently, the clinician also advances and secures a second retractor body 220 into the patient, e.g., superior or inferior relative to the first retractor body, while in the folded configuration in the same manner as the first retractor body 220. Again, as with the previously described method embodiment, in some alternative variations, the pin may be inserted into the vertebral bone structure prior to the retractor body 220 for either or both retractor bodies when performing the method.

Once both retractor bodies are secured to a respective vertebra, each extension panel is rotated outward relative to a respective main panel by hand, for example, moving extension panels on each side of a main panel in a medial or lateral direction until the opposing expansion panels of the respective retractor bodies overlap one another. n some examples, when the insertion instrument 300 is removed, the extension panels may be actively manipulated, e.g., by hand or with a tool, to expand the retractor body 220 to a U-shaped or other open configuration, i.e., second configuration. In other examples, the hinges of the retractor body are biased so that upon release from the instrument 300, the extension panels passively expand to convert the retractor body to a neutral state defined by a U-shape or other open configuration.

To fix opposing retractor bodies 220 in a superior-inferior direction, the locking arms 70 may be secured to overlapping extension panels 240, 250. Again, as with other method embodiments described herein, a retractor such as a Gelpi retractor may be used to maintain a medial-lateral dimension of the portal formed by the retractor system. Prongs of the retractor may be inserted into the bores of the extension panels to hold the retractor in place.

At this time, a surgical procedure may be performed within the portal created by the retractor bodies. For example, a cervical plate may be inserted and then secured to the spine. Upon completion of the surgical procedure, the retractor system 200 may be removed from the surgical site.

The method of using the retractor system may be varied in many ways. For example, when the retractor assembly 10 is advanced to the surgical site adjacent to the spine, it may be inserted without the pins. Then, once aligned with the desired positions on the vertebrae, the pins may be inserted through the retractor bodies and into bone prior to the retraction step. Insertion may be through prepared holes in the vertebrae. Alternatively, self-tapping pins may be used and anchored into the bone without prepared holes. Both the pins and self-tapping pins may be slid through sleeves on the retractor bodies. In another example, each retractor body may be separately advanced to the surgical site, one at a time.

In some examples, one or both of the retractor bodies may be inserted in the flat configuration initially, and then converted into the configuration for overlapping with an opposite retractor body, e.g., U-shaped configuration, while within the patient and adjacent to the spine. In some examples, the retractor bodies are configured for active means of expansion. For instance, manual manipulation by hand or a tool or tools may be used to convert the retractor body from a flat or folded configuration to an open configuration. The tool may be any tool that may be used to access the retractor bodies in the patient and include features to push or manipulate the extension panels relative to the main panel. In other examples, the retractor bodies are biased in the open position and are held closed by force during insertion. In these examples, the forces are released when the retractor body is advanced to a desired position, and the retractor body expands to the open position. In some examples, a retractor as known to those of ordinary skill in the art is used to create an initial opening to temporarily provide additional space to aid in the advancement of one or more retractor bodies into the surgical site while in the U-shaped configuration. In this manner, no transition from the first flat configuration to the second U-shaped configuration is required.

In some examples, with the full retractor system including two retractor bodies in position, two locking arms, one on each side of the combined structure, are used to fix a spacing between the main panels of each body. In another example, a total of four locking arms may be used, with two on each side. Other variations are also contemplated and may be desirable as a function of the surgical conditions.

In some examples with retractor bodies having more than two extension panels, a clinician may remove one or more of the extension panels prior to insertion into the patient to suit the particular surgical conditions. For instance, if the size of a required surgical portal is much less than what could be created using two retractor bodies each having four extension panels (two on each side), then the two panels at the ends may be removed so that there are only two extension panels in total on each retractor body.

In still further examples, a drill guide (not shown) may optionally be utilized to locate insertion points for the fixation pins prior to the insertion of the fixation pins. Specifically, the drill guide may be inserted through the indicator pin such that the drill guide is in registration with the vertebral bodies. At this time, a drill (not shown) may be utilized to form holes in the vertebral bodies to receive the respective fixation pins.

In some examples, the method of the present disclosure may be performed for other procedures involving the spine or in an anatomical region other than the spine. For instance, the retractor system may be used to create access to the spine for the placement of an intervertebral implant. In this procedure, once a surgical portal is created using the methods described herein, a distraction device is used to hold adjacent vertebrae apart. Then, the applicable intervertebral disc space is cleared and an implant may be inserted. The distraction tool may be removed once the implant is in the proper position and it is safe for the adjacent vertebrae to bear on the implant. Reference may be made to U.S. Pat. No. 9,017,409, the entire contents of which are incorporated herein by reference, for one example of a detailed description of the construction and operation of an implant device.

In another aspect, two or more of the above retractor bodies, fixation pins and locking arms, or other structures to hold together the retractor bodies, may be included together as a kit. In one embodiment, a kit is contained in a single package as a system or in multiple packages that may be selected as needed by the operator to form a system. For example, such a kit may include two retractor bodies, two pins and two locking arms. If the kit includes more than one retractor body, the plurality of retractor bodies may vary in overall size, relative dimensions among the panels, materials, or the like, from which the most suitable retractor bodies may be chosen for a particular surgical procedure. Any combination of retractor bodies, fixation pins and locking arms may also be included in a single package or in separate packaging which are later brought together as a kit.

The kit may be varied in many ways. For example, it is contemplated that any combination of the components contemplated in the present disclosure may be included as part of a kit. This may be in the form of a kit of the above embodiments combined with one or more of an insertion instrument, tools for manipulating the retractor bodies from the first to the second configuration, a Gelpi spreader, a retractor and/or other devices that aid in the placement and securement of the retractor system. Such components may be included as single elements or more than one may be included as part of the kit. Additionally, to the extent other tools or devices are used in conjunction with the devices described herein, such tools or devices may also be included in the kit. The various combinations of components of any contemplated kit may be included in a single package or distributed among multiple packages. In other examples, the kits contemplated herein may be accompanied by an instruction manual on how to perform one or more of the methods of using the contents of the kit.

It should be noted that any of the devices and methods disclosed herein can be used in conjunction with robotic technology. For example, any of the retractor bodies or insertion instruments described herein can be used with robotic surgical systems to perform a retraction procedure. The retractor bodies can be advanced and/or manipulated with a robotic system or a robotic arm to position the retractor body and alter the configuration of the retractor body (e.g., flat to open U-shape) during a procedure. Further, any or all of the steps described in the methods for performing a retraction procedure of the present disclosure may be performed using a robotic system.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A retractor system comprising:
   first and second fixation pins; and
   a retractor assembly including first and second retractor bodies, the first retractor body including a first main panel and first and second extension panels extending from the first main panel, the second retractor body including a second main panel and third and fourth extension panels extending from the second main panel, the first and second main panels including a sleeve defining a bore dimensioned to receive one of the first and second fixation pins, and the first and third extension panels including a plurality of bores,
   wherein the first and second retractor bodies are transitionable between a first configuration in which each of the first and second retractor bodies is substantially flat, and a second configuration in which the first and second extension panels are transverse to the first main panel and the third and fourth extension panels are transverse to the second main panel such that the extension panels of each retractor body oppose each other,
   wherein the first and second extension panels are configured to selectively overlap the respective third and fourth extension panels in predetermined increments when the first and second retractor bodies are in the second configuration, whereby the first and second main panels are transitionable between a first position where a first bore of the plurality of bores in the first extension panel is aligned with a first bore of the plurality of bores in the third extension panel, and a second position where a second bore of the plurality of bores in the first extension panel is aligned with a second bore of the plurality of bores in the third extension panel, the first and second main panels being closer to each other in the first position than in the second position, and the respective bores of the overlapping first and third extension panels being configured to receive a peg to lock the first and third extension panels together.

2. The retractor system according to claim 1, wherein in the second configuration, the first and second extension panels are parallel to one another.

3. The retractor system according to claim 1, wherein in the second configuration, each of the first and second retractor bodies have a substantially U-shaped profile.

4. The retractor system according to claim 1, wherein each main panel includes a base portion and an extension portion extending proximally from the base portion, the extension portion being more flexible than the base portion.

5. The retractor system according to claim 1, further comprising a locking arm having an elongate member and a peg dimensioned to be received in overlapping bores of the first and third extension panels in order to securely lock the relative position of the first and second retractor bodies.

6. The retractor system according to claim 1, wherein the main panel and the extension panels are together formed monolithically for each retractor body.

7. The retractor system according to claim 1, wherein at least one of the main panels defines a curvature.

8. The retractor system according to claim 1, wherein at least one of the first or second fixation pins includes a distal portion having threads configured to threadably engage a vertebral body and a proximal portion having a key feature configure to provide non-slip engagement with a driver to drive the at least one of the first or second fixation pins.

* * * * *